(12) United States Patent
Sun

(10) Patent No.: US 10,352,892 B2
(45) Date of Patent: Jul. 16, 2019

(54) ELECTRODE FOR TRACE OXYGEN SENSOR

(71) Applicant: TELEDYNE INSTRUMENTS, INC., Thousand Oaks, CA (US)

(72) Inventor: Zhenhe Sun, Corona, CA (US)

(73) Assignee: TELEDYNE INSTRUMENTS, INC., Thousand Oaks, CA (US)

( * ) Notice: Subject to any disclaimer, the term of this patent is extended or adjusted under 35 U.S.C. 154(b) by 216 days.

(21) Appl. No.: 15/248,988

(22) Filed: Aug. 26, 2016

(65) Prior Publication Data

US 2018/0059047 A1    Mar. 1, 2018

(51) Int. Cl.
*G01N 27/413* (2006.01)
*G01N 27/404* (2006.01)
*G01N 27/403* (2006.01)

(52) U.S. Cl.
CPC ......... *G01N 27/404* (2013.01); *G01N 27/403* (2013.01); *G01N 27/413* (2013.01)

(58) Field of Classification Search
CPC ... G01N 27/413; G01N 27/404; G01N 27/403
See application file for complete search history.

(56) References Cited

U.S. PATENT DOCUMENTS 5,560,999 A * 10/1996 Pedicini ................ H01M 6/50
429/407
5,652,068 A * 7/1997 Shuster ................ H01M 12/06
429/407

FOREIGN PATENT DOCUMENTS

DE      2352042 A1 *  5/1975  .......... H01M 10/399
GB      1450776 A  *  9/1976  .......... G01N 27/4045

* cited by examiner

*Primary Examiner* — Edward J. Schmiedel
(74) *Attorney, Agent, or Firm* — McGuireWoods LLP

(57) ABSTRACT

An apparatus and a method for a trace oxygen sensor is configured with a floating cathode that has a capability to detect part-per-billion (ppb) level or less of oxygen in a gas background. An electrolyte reservoir can supply electrolyte when electrolyte level is low. An electrolyte reservoir may be connected to the main cell along with a protection electrode.

12 Claims, 5 Drawing Sheets

ELECTRODE FOR TRACE OXYGEN SENSOR

BACKGROUND

1.0 Field of the Disclosure

The present disclosure generally relates to an apparatus and a method for a trace oxygen sensor and, more particularly, the present disclosure generally relates to an apparatus and a method for a trace oxygen sensor that is configured with a floating cathode that has a capability to detect parts-per-billion (ppb) level of oxygen, among other features

2.0 Related Art

In existing trace oxygen sensors, such as a Hersch cell, the cathode is normally submersed in the electrolyte or wetted with a wetting support material and open directly to a gas sample. No sensing membrane or any type of gas barrier is used between the gas sample and the electrode. Water from the electrolyte solution may evaporate, especially if the gas sample is very dry. As a consequence, the sensor's performance will deteriorate as the electrolyte level changes. In an existing trace oxygen analyzer, a complicated moisture maintenance system is required to insure that the sample gas moisture level remains constant and keep electrolyte level stable.

Some oxygen analyzers employ a humidifier and a water reservoir tank as the on-board moisture maintenance system. The system needs to be temperature controlled to have a constant moisture level in the cell and in the gas sample. This technique is cumbersome and expensive and it can accurately detect oxygen reliably only in the parts-per-million range.

A typically commercially available trace oxygen sensor such as in a Hersch cell has two electrodes and a liquid electrolyte, a treated silver (Ag) mesh as cathode and a metal lead (Pb) as anode, and a KOH solution is the typical electrolyte solution. A gas sample containing trace amount of oxygen is introduced to the cathode, and oxygen from the sample is electrochemically reduced at the cathode and at the same time, anode is electrochemically oxidized into lead oxide.

Generally, the electrochemical reactions at the cathode and at the anode may be as follows.

At the cathode:

$$O_2 + 2H_2O + 4e^- \rightarrow 4OH^- \tag{1}$$

At the anode:

$$Pb + 2OH^- \rightarrow PbO + H_2O + 2e^- \tag{2}$$

The over-all reaction is:

$$2Pb + O_2 \rightarrow 2PbO \tag{3}$$

This electrochemical reaction generates a current between cathode and anode and is proportional to oxygen concentration in the sample gas. This current can be processed by any means of electronics, such as conversion, amplification and digitalization. The data, then, can be used to display oxygen content or to data acquisition system for recording.

A better approach to eliminate a need for humidifiers and a better configuration to substantially improve oxygen detect capability would be a useful improvement to electrochemical oxygen sensors.

SUMMARY OF THE DISCLOSURE

The system and method of the disclosure overcomes the problems described above and may eliminate the need for a complicated moisture maintenance system for an oxygen gas analyzer since the cathode can freely change position as the electrolyte level varies, while also covering a substantial portion of the electrolyte surface thereby minimizing electrolyte loss. Moreover, the amount of contact area between the cathode and the electrolyte is always kept constant as it floats, even as the level of electrolyte changes.

In one aspect, an electrochemical oxygen sensor includes a main cell configured to hold an electrolyte and to receive a sample gas, a first cathode configured to float on the electrolyte, a first anode configured to be in contact with the electrolyte, wherein the first cathode and first anode are connectable to electronics to receive an electrical signal indicative of a level of oxygen in the sample gas. The electrolyte reservoir may be arranged to permit electrolyte flow from the electrolyte reservoir to the main cell. The electrochemical oxygen sensor may further comprise a second cathode and a second anode configured in the electrolyte reservoir to prevent dissolved oxygen in the electrolyte reservoir from entering the main cell. The first cathode, first anode, second cathode and second anode may be connectable to current signal processing electronics. The electrochemical oxygen sensor may further comprise a flexible connector connected to the first cathode and a cathode connector, the flexible connector sufficiently flexible and of a sufficient length to permit the first cathode to move as a level of the electrolyte changes while remaining electrically operative. A contact area of the first cathode with the electrolyte may remain constant as the electrolyte level changes. The first cathode may be configured to have, and to be in contact with, a surface area of 50% or more of a surface area of the electrolyte held by the main cell. The first cathode may be configured to have, and to be in contact with, a surface area of about 60% to about 90% of surface area of the electrolyte. The electrochemical oxygen sensor may detect oxygen in the sample gas of 10 ppb or less.

In one aspect, an electrochemical oxygen sensor includes a main cell configured to hold an electrolyte and to receive a sample gas, an electrolyte reservoir configured to contain a reserve of the electrolyte and fluidly connected to the main cell, a first cathode configured to float on the electrolyte in the main cell, a first anode configured to be in contact with the electrolyte in the main cell, a second anode in contact with the electrolyte in the electrolyte reservoir and a second cathode in contact with the electrolyte between the main cell and the reservoir, the first cathode and the first anode are configured to be connectable to electronics, the first cathode and first anode configured to provide an electrical signal indicative of a level of oxygen in the sample gas, and the second anode and second cathode configured to prevent dissolved oxygen in the electrolyte reservoir from entering the main cell. The electrochemical oxygen sensor may further comprise a flexible connector connected to the first cathode, the flexible connector sufficiently flexible and of a sufficient length to permit the first cathode to move vertically as a level of the electrolyte changes in the main cell. A contact area of the first cathode with the electrolyte may remain constant as the electrolyte level changes in the main cell. The first cathode may be configured to have, and to be in contact with, a surface area of 50% or more of a surface area of the electrolyte held by the main cell. The first cathode may be configured to have, and to be in contact with, a surface area of about 50% to about 90% of surface area of the electrolyte. The electrochemical oxygen sensor may detect oxygen in the sample gas of 100 ppb or less.

In one aspect, a method for detecting oxygen levels in a gas sample includes providing a first cathode that is configured to float on an electrolyte held within a main cell, connecting a flexible connector to the first cathode of sufficient length and sufficient flexibility to permit vertical movement of the first cathode as a level of the electrolyte changes; and providing a first anode configured to be in contact with the electrolyte, wherein the first cathode is configured to have a constant area of contact with the electrolyte as a level of electrolyte changes, and the first cathode and first anode are connectable to electronics for detecting an amount of oxygen in a sample gas flowing within the main cell. The first cathode and first anode may be connectable to electronics for detecting presence of oxygen in a sample gas at levels of 100 ppb or less. The method may further comprise providing an electrolyte reservoir in fluid connection with the main cell to provide a reserve of electrolyte. The method may further comprise providing a second cathode and a second anode to prevent dissolved oxygen in the electrolyte reservoir from entering the main cell. The method may further comprise connecting electronics to receive output of the first cathode and the first anode to determine the amount of oxygen in the sample gas.

Additional features, advantages, and embodiments of the disclosure may be set forth or apparent from consideration of the detailed description and drawings. Moreover, it is noted that the foregoing summary of the disclosure and the following detailed description and drawings provide non-limiting examples of the disclosure, which are intended to provide explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

Figure 1:
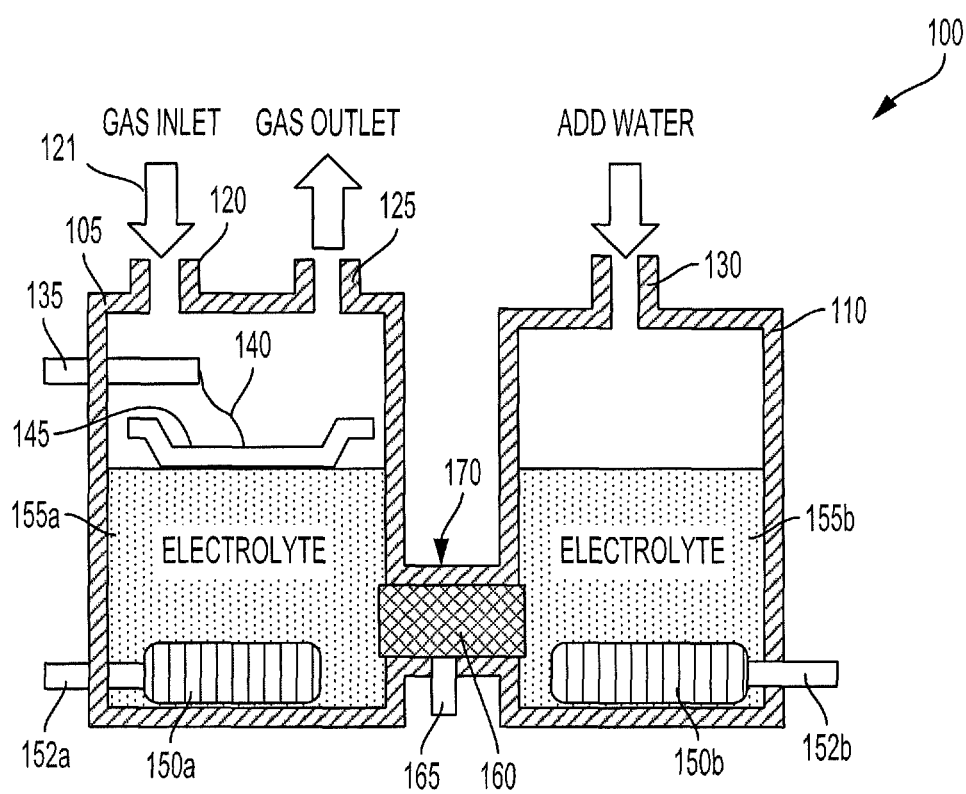
FIG. 1 is an example of an electrochemical oxygen sensor, configured according to principles of the disclosure.

The present disclosure is further described in the detailed description that follows.

DETAILED DESCRIPTION OF THE DISCLOSURE

The disclosure and the various features and advantageous details thereof are explained more fully "with reference to the non-limiting embodiments and examples that are described and/or illustrated in the accompanying drawings and detailed in the following description. It is noted that the features illustrated in the drawings and attachment are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

A "computer," as used in this disclosure, means any machine, device, circuit, component, or module, or any system of machines, devices, circuits, components, modules, or the like, which are capable of manipulating data according to one or more instructions, such as, for example, without limitation, a processor, a microprocessor, a programmable logical controller, a controller, a central processing unit, a general purpose computer, a super computer, a personal computer, a laptop computer, a palmtop computer, a notebook computer, a cloud computer, a desktop computer, a workstation computer, a server, or the like, or an array of processors, microprocessors, central processing units, general purpose computers, super computers, personal computers, laptop computers, palmtop computers, notebook computers, desktop computers, workstation computers, servers, or the like.

A "database," as used in this disclosure, means any combination of software and/or hardware, including at least one application and/or at least one computer. The database may include a structured collection of records or data organized according to a database model, such as, for example, but not limited to at least one of a relational model, a hierarchical model, a network model or the like. The database may include a database management system application (DBMS) as is known in the art. The at least one application may include, but is not limited to, for example, an application program that can accept connections to service requests from clients by sending back responses to the clients. The database may be configured to run the at least one application, often under heavy workloads, unattended, for extended periods of time with minimal human direction.

A "communication link," as used in this disclosure, means a wired and/or wireless medium that conveys data or information between at least two points. The wired and/or wireless medium may include, for example, a metallic conductor link, a radio frequency (RF) communication link, an Infrared (IR) communication link, an optical communication link, or the like, without limitation. The RF communication link: may include, for example, Ethernet, WiFi, WiMAX, IEEE 802.11, DECT, 0G, 1G, 2G, 3G or 4G cellular standards, Bluetooth, and the like.

The terms "including," "comprising," and variations thereof, as used in this disclosure, mean "including, but not limited to," unless expressly specified otherwise.

The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

In one aspect, a floating gas sensing electrode, instead of a traditional submersed electrode, is used in the oxygen sensor of this present disclosure. The oxygen sensor, a type of galvanic cell, is configured with a floating cathode that has sufficient buoyancy to float on an electrolyte and has the capability to detect ppb (parts-per-billion) level of oxygen in a gas sample. The primary purpose of the floating cathode is to electrochemically reduce oxygen in a sample gas, i.e., the gas being sampled for detection of an amount of oxygen content. An electrolyte reservoir, that can supply electrolyte when electrolyte level is low, may be connected to the main cell. A protection electrode may also be employed. In one aspect, an apparatus comprising a floating cathode and a flexible connector connected to the floating cathode is provided. The flexible connector may be of sufficient flexibility and length to permit the floating cathode to rise and fall as a level of electrolyte, upon which the floating cathode is in contact, rise or falls.

According to principles of this disclosure, a high stable contact area between the floating cathode and electrolyte is maintained making current output between the cathodes and the anodes much more stable than existing traditional sub-immersed cathode designs. In existing traditional sub-immersed designs, a certain percentage of the cathode is immersed inside the electrolyte that cannot be used, but still contributes to resident current that is not favorable for trace oxygen detection.

FIG. 1 is an example of an electrochemical oxygen sensor 100, configured according to principles of the disclosure. The electrochemical oxygen sensor 100 may comprise a main cell body 105 and an electrolyte reservoir 110 in fluid communication with one another via a liquid passage 170. A gas inlet 120 permits sample gas, denoted by arrow 121 to flow through the main cell 105. The flow of sample gas 121 contacts a gas sensing electrode, namely, floating cathode 140. The flow of sample gas 121 may exit out gas outlet 125.

A flexible connector 140 may connect the floating cathode 145 to a cathode connector 135 of the electrochemical oxygen sensor 100. The cathode connector 135 may be configured in a wall of the main cell 105 to permit external electronics, e.g., current signal process electronics 200 (FIG. 4), to connect to the floating cathode 140. The cathode connector 135 may be configured in a wall of the main cell 105 to maintain a water tight seal. The flexible connector 140 may be sufficiently flexible and of a sufficient length to maintain electrical connectivity with the floating cathode 140 as the floating cathode rises or falls vertically within the main cell 105 due to changes in electrolyte 155a level.

The floating cathode 140 may be in the shape of a disk or other shape in order to assist in floating capability. For example, the shape may include an oval, a circular shape, an irregular shape, a partial circular shape, a rectangle shape, a square shape, a shape having curves, a Lotus-flower type shape, or the like.

Figure 4:
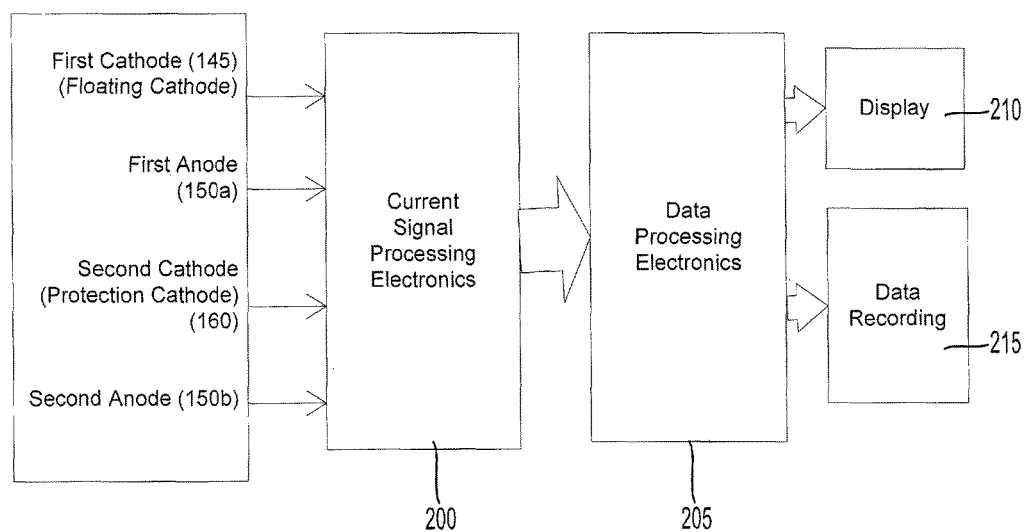
FIG. 4 is an example block diagram of connectivity of the cathodes and anodes with electronics, according to principles of the disclosure.

The electrochemical oxygen sensor 100 may further comprise first anode 150a with connector 152a configured in main cell 105 and a second anode 150b with connector 152b configured in electrolyte reservoir 110. The first anode 150a and second anode 152b may be configured to be submersed in electrolyte 155a, 155b. Moreover, connectors 152a, 152b may be configured in a wall of the main cell 105 and the electrolyte reservoir 110, respectively. Connectors 152a, 152b may be configured in and through the respective walls to maintain a water tight seal while permitting connection to external electronics, e.g., current signal process electronics 200 (FIG. 4).

The electrochemical oxygen sensor 100 may further comprise a second cathode 160, which may be a blocking or protection cathode. The second cathode 160 and a second anode 150b configured in the electrolyte reservoir may be configured to prevent dissolved oxygen in the electrolyte reservoir from entering the main cell. The second cathode 160 may be configured proximate, along, or in the passage-way 170. A connector 165 may connect the protection cathode 160 to external electronics, e.g., current signal process electronics 200 (FIG. 4). In some embodiments, the second anode 150b and second cathode 160 may not be required.

The electrolyte 155a, 155b may be, e.g., potassium hydroxide (KOH), sodium hydroxide (NaOH), potassium bicarbonate ($KHCO_3$), potassium acetate (KAc), or a mixture thereof, in any practical combination. The concentration of electrolyte 155a, 155b may be from about 10% to 30%, about 10-20%, about 15-20%, about 15-25%, about 15-30% (w/v %, weight per volume). The concentration of electrolyte 155a, 155b may be any specific percentage (+/−5%) within the range of about 10% to about 30% (w/v %, weight per volume). For example, the concentration of electrolyte 155a, 155b may be 15%, 20%, 25% (w/v %, weight per volume). In some embodiments, the concentration of electrolyte 155a, 155b may be more than 30% or less than 15% (w/v %, weight per volume).

This oxygen sensor 100 of the present disclosure eliminates the need of a complicated moisture maintenance system since the floating cathode 145 can freely float and change position as the electrolyte level changes, and minimize evaporation b substantially covering the electrolyte itself. Further, the contact area between the floating cathode 145 and the electrolyte 155a is always kept constant as it floats upon the liquid electrolyte 155a. The surface area of the floating cathode in contact with the electrolyte 155a may be maximized while also significantly reducing the rate of evaporation of the electrolyte 155a. As a result of this configuration, the noise level from the floating cathode 145 is significantly reduced and allows the sensor 100 to accurately measure oxygen in the ppb (parts-per-billon) range for the gas sample 121. Additional electrolyte 155b may be added into the electrolyte reservoir 110 via port 130. The addition of electrolyte 155b may be a manual or automatic process.

Figure 2:
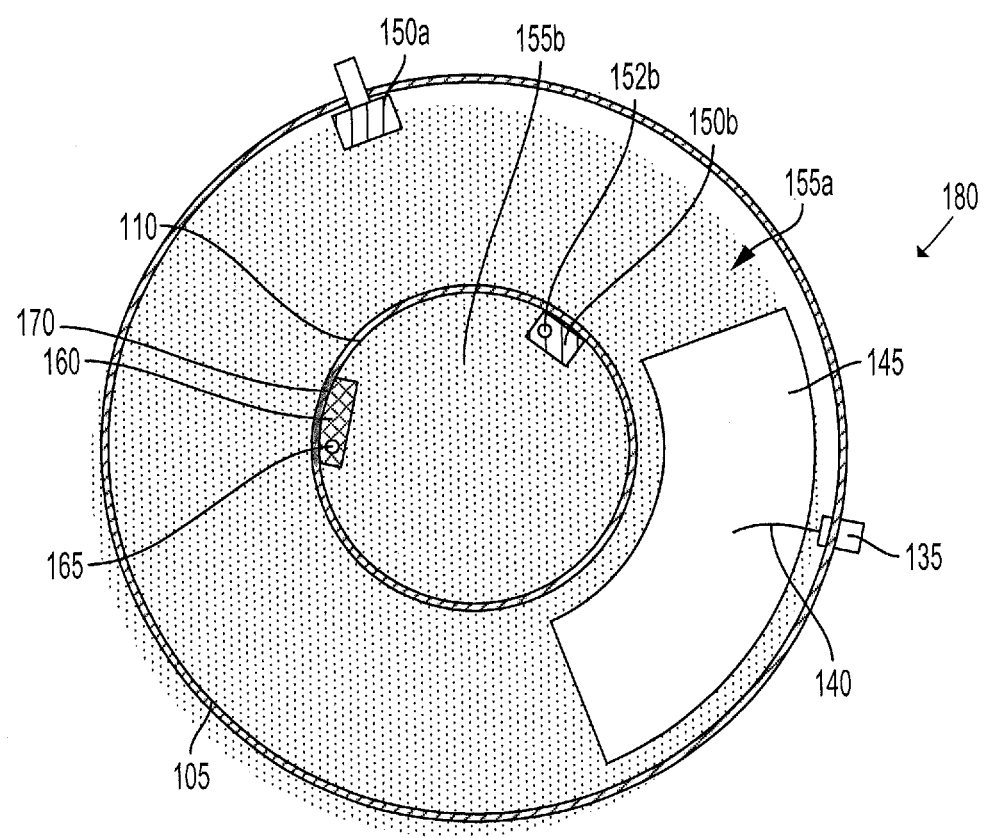
FIG. 2 is a top view of an example of an electrochemical oxygen sensor, configured according to principles of the disclosure.

FIG. 2 is a top view of an example of an electrochemical oxygen sensor 180, configured according to principles of the disclosure. The principle of operation of electrochemical oxygen sensor 170 is the same as for the electrochemical oxygen sensor 100, except for a different configuration. In FIG. 2, the electrochemical oxygen sensor 170 is configured so that the main cell 105 is circular and the electrolyte reservoir 110 is also circular. The floating cathode 145 may float in the area between the main cell 105 and the electrolyte reservoir 110. The floating cathode 145 may take any shape that fits into the area between the main cell 105 and the electrolyte reservoir 110. The more surface area of the floating cathode 145, the lower the rate of loss of electrolyte. The more surface area of the floating cathode 145, the more sensitivity of the oxygen sensor 170. Other shapes of the main cell 105 and the electrolyte reservoir 110 may be possible. The floating cathode 145 may be configured to have, and to be in contact with, a surface area of 50% or more of the main cell electrolyte surface area. The floating cathode 145 may be configured to have, and to be in contact with, a surface area of about 50% to about 90% of the main cell electrolyte surface area. The floating cathode 145 may be configured to have, and to be in contact with, a surface area of about 60% to about 90% of the main cell electrolyte surface area. The floating cathode 145 may be configured to have, and to be in contact with, a surface area of about 70% to about 90% of the main cell electrolyte surface area. The floating cathode 145 may be configured to have, and to be in contact with, a surface area of about 80% to about 90% of the main cell electrolyte surface area. The floating cathode 145 may be configured to have, and to be in contact with, a surface area of less than 50% of the main cell electrolyte surface area. The floating cathode 145 may be configured to have, and to be in contact with, a surface area of more than about 90% of the main cell electrolyte surface area.

The body, i.e., walls and bottom, of the main cell 105 and/or electrolyte reservoir 110 may be made with any type material such as plastic that is tolerant to the electrolyte (e.g., KOH, NaOH, $KHCO_3$ or KAc), and has low oxygen permeation rate. The material may be, e.g., Acrylic, Nylon, ABS, High Density Polyethylene (HDPE), PVC, or the like.

The cathodes 145, 160 may be made with any type of high surface area gas sensing electrode material, such as a porous metal (e.g., silver, gold, platinum, palladium, or rhodium) membrane, gas diffusion electrode (for fuel cell with silver, gold, platinum catalyst), perforated or etched metal mesh, or the like. The anodes 150a, 150b may be, e.g., lead (Pb), cadmium (Cd), zinc (Zn), copper (Cu), Tin (Sn) and their alloys, in the forms of, e.g., foil, sheet, disk, or wires.

The electrochemical oxygen sensor 100, 180 may reliably detect oxygen in a gas sample of 10 ppb, or less. The electrochemical oxygen sensor 100, 180 may reliably detect oxygen in a gas sample of 100 ppb, or less. The electrochemical oxygen sensor 100, 180 may reliably detect oxygen in a gas sample of 10 ppb to 50 ppb. The electrochemical oxygen sensor 100, 180 may reliably detect oxygen in a gas sample of 10 ppb to 80 ppb. The electrochemical oxygen sensor 100, 180 may reliably detect oxygen in a gas sample of 100 ppb, or more.

Figure 3A:
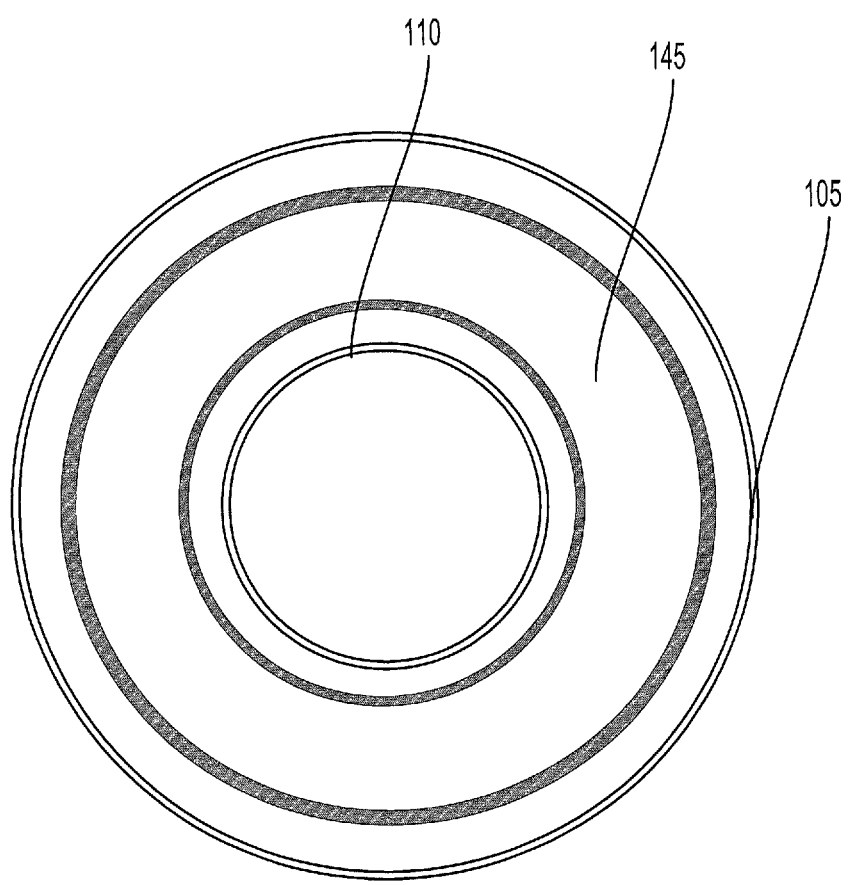
FIG. 3A is an illustration showing an example of a configuration of a floating electrode in the area between the main cell and the electrolyte reservoir.

FIG. 3A is an illustration showing an example of a configuration of a floating electrode 145 in the area between the main cell 105 and the electrolyte reservoir 110. In this example, the floating cathode 145 surrounds the electrolyte reservoir 110. The other components of the electrochemical oxygen sensor may be arranged in a similar operational fashion as shown in FIG. 2.

Figure 3B:
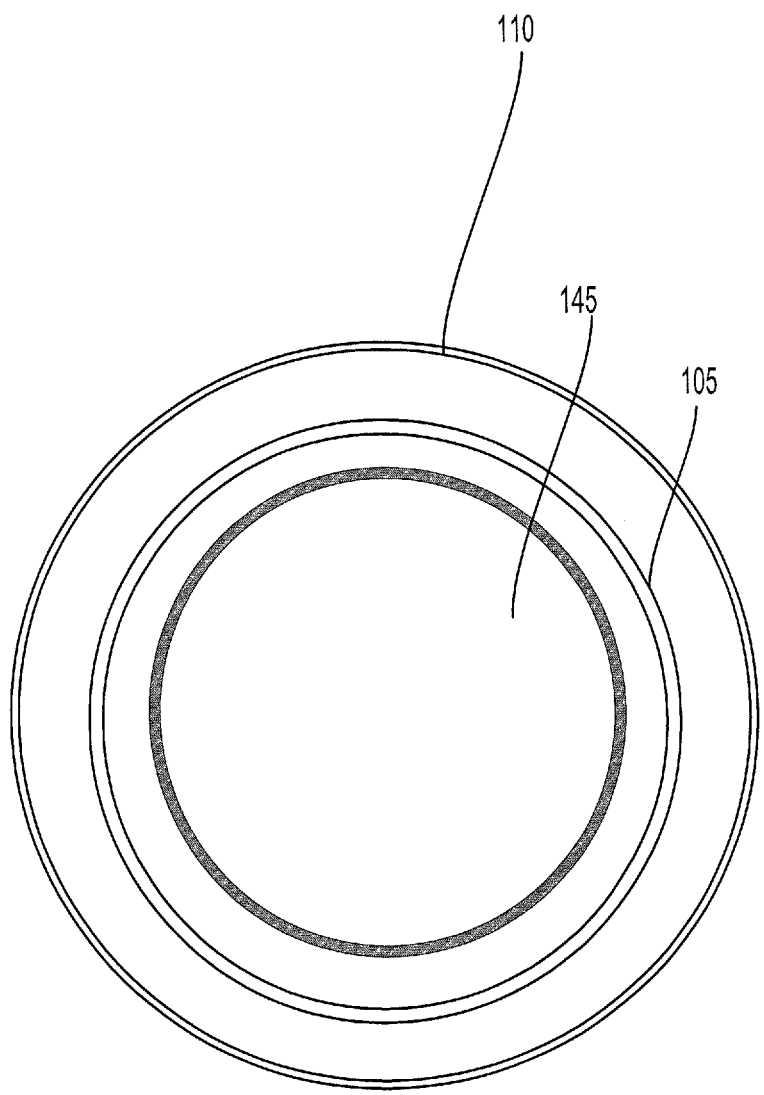
FIG. 3B is an illustration showing an example of a configuration of a floating electrode 145 within the main cell 105.

FIG. 3B is an illustration showing an example of a configuration of a floating electrode 145 within the main cell 105. The main cell configured within the electrolyte reservoir 110. The other components of the electrochemical oxygen sensor may be arranged to provide equivalent function as in FIG. 1 or FIG. 2. For example, liquid passage 170 may be arranged to permit electrolyte to pass from the electrolyte reservoir 110 to the interior main cell 105. The electrodes may be positioned in equivalent functional locations.

The arrangements of FIG. 1, FIG. 2, FIGS. 3A and 3B permit the floating cathode 145 to operate by floating in the main cell with a reservoir supplying added electrolyte as needed. The floating cathode 145 reduces or minimizes electrolyte evaporation by covering a substantial portion of the electrolyte surface. Therefore, added humidification is not necessary. The electrolyte reservoir 110 may be configured within the main cell 105. The electrolyte reservoir 110 may be configured to surround the main cell 105. The electrolyte reservoir 110 may be configured to be external and separate but connected to the main cell 105.

FIG. 4 is an example block diagram of connectivity of the cathodes 145, 160 and anodes 150a, 150b with electronics, according to principles of the disclosure. The first cathode 145, the first anode 150a, the second cathode 160 and the second anode 150b may be connected by a communication link to current signal processing electronics 200. The current signal processing electronics 200 may also provide power to the electrodes. The current signal processing electronics 200 may convert received electrical signals to equivalent digital signals and levels. Data processing electronics 205 may receive the digital signals and levels output from the current signal processing electronics 200 over a communication link. Data processing electronics 205 may comprise a computer or a server and may determine oxygen level of the sample gas 121. Data processing electronics 205 may output over a communication link information related to the determine oxygen level of the sample gas 121 on a display 210. The display 210 and/or data processing electronics 205 may be connected to a network. Moreover, data processing electronics 205 may output over a communication link information related to the determine oxygen level of the sample gas 121 to a data recording device 215, which may comprise a database.

This present disclosure may employ four electrodes, i.e. first cathode 145 (i.e., floating cathode), first anode 150a, second cathode 160, and second anode 150b. In some embodiments, only the first cathode 145 and the first anode 150a may be employed. All four electrodes may be connected to the signal process electronics 200. The first cathode 145 and first anode 150a form a first pair to permit current flow between them. The second cathode 160 and second anode 150b form a second pair permitting another (second) current flow between them. The current flow between first pair (i.e., first cathode 145 and first anode 150a) may be used to measure oxygen concentration in the sample gas 121. The current flow between second pair (i.e., the second cathode 160 and second anode 150b) may be used to show a need to add water to the electrolyte reservoir 110 or, alternatively, may be simply shorted when connected to the electronics. The second pair may be used asynchronously to the first pair. The second pair may comprise a low water level detector and the signal may be detected by the current signal processing electronics 200, which may communicate the low water condition to the data signal processing electronics 205 for eventual communicating to a user at display 210. A user may then replenish water in the electrolyte reservoir 110.

A wide range of electronics means of converting current to voltage can be used to process the current output signal, as is known in the art. The voltage signal converted from current signal can be amplified and digitized for any digital processing, such as calibration, storage, and transfer. The data can be displayed on screen or recorded.

The electrochemical oxygen sensor configured according to principles of the disclosure may be used in most applications where detection of oxygen in a gas sample is required. For example, when used in, e.g. wafer chip production, the electrochemical oxygen sensor configured according to principles of the disclosure permits finding oxygen impurity, such as may be found within the ultra-high purity (UHP) bulk gases requirement of wafer chip production, to be detected to below about 10 ppb in order to ensure a high wafer yield. For the reasons noted above, traditional existing sensors have difficulty in achieving this level of sensitivity or lower detection limit.

In petrochemical industries, some chemical reactions are very sensitive to low oxygen concentration. Oxygen present in those reactions will yield low production yield. Some catalyst, in chemical production, can be damaged by even trace oxygen. In some cases, oxygen will act as a catalyst to start polymerization reaction. In those cases, monitoring oxygen is very important for prevention off-specification products and unwanted reaction, for which the oxygen sensor configured according to principles of this disclosure provides greater performance.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications or modifications of the disclosure. Moreover features of one example or embodiment may be employed with other examples or embodiments.

What is claimed:

1. An electrochemical oxygen sensor comprising:
   a main cell configured to hold an electrolyte and to receive a sample gas;
   a first cathode comprising a porous metal membrane or a gas diffusion electrode configured to float on the electrolyte;
   a first anode configured to be in contact with the electrolyte, wherein the first cathode and first anode are connectable to electronics to receive an electrical signal indicative of a level of oxygen impurity in the sample gas;
   an electrolyte reservoir arranged to permit electrolyte flow from the electrolyte reservoir to the main cell;
   a second cathode and a second anode configured in the electrolyte reservoir to prevent dissolved oxygen in the electrolyte reservoir from entering the main cell; and
   wherein the first cathode, first anode, second cathode, and second anode are connectable to current signal processing electronics.

2. The electrochemical oxygen sensor of claim 1, further comprising a flexible connector connected to the first cathode and a cathode connector, the flexible connector sufficiently flexible and of a sufficient length to permit the first cathode to move as a level of the electrolyte changes while remaining electrically operative.

3. The electrochemical oxygen sensor of claim 1, wherein a contact area of the first cathode with the electrolyte remains constant as a level of the electrolyte changes.

4. The electrochemical oxygen sensor of claim 1, wherein the first cathode is configured to have, and to be in contact with, a surface area of 50% or more of a surface area of the electrolyte held by the main cell.

5. The electrochemical oxygen sensor of claim 4, wherein the first cathode is configured to have, and to be in contact with, a surface area of about 60% to about 90% of surface area of the electrolyte.

6. The electrochemical oxygen sensor of claim 1, wherein the electrochemical oxygen sensor detects oxygen in the sample gas of 10 ppb or less.

7. The electrochemical oxygen sensor of claim 1, wherein a gas inlet and a gas outlet is configured in the main cell permitting the sample gas to enter the main cell from the gas inlet to flow across the floating first cathode and out the gas outlet.

8. An electrochemical oxygen sensor comprising:
   a main cell configured to hold an electrolyte and to receive a sample gas;
   an electrolyte reservoir configured to contain a reserve of the electrolyte and fluidly connected to the main cell;
   a first cathode configured to float on the electrolyte in the main cell;
   a first anode configured to be in contact with the electrolyte in the main cell;
   a second anode in contact with the electrolyte in the electrolyte reservoir; and
   a second cathode in contact with the electrolyte between the main cell and the electrolyte reservoir,
   the first cathode and the first anode are configured to be connectable to electronics, the first cathode and first anode configured to provide an electrical signal indicative of a level of oxygen in the sample gas, and the second anode and second cathode configured to prevent dissolved oxygen in the electrolyte reservoir from entering the main cell,
   wherein the electrochemical oxygen sensor detects oxygen in the sample gas of 100 ppb or less.

9. The electrochemical oxygen sensor of claim 8, wherein a contact area of the first cathode with the electrolyte remains constant as a level of the electrolyte changes in the main cell.

10. An electrochemical oxygen sensor comprising:
    a main cell configured to hold an electrolyte and to receive a sample gas;
    an electrolyte reservoir configured to contain a reserve of the electrolyte and fluidly connected to the main cell;
    a first cathode configured to float on the electrolyte in the main cell;
    a first anode configured to be in contact with the electrolyte in the main cell;
    a second anode in contact with the electrolyte in the electrolyte reservoir; and
    a second cathode in contact with the electrolyte between the main cell and the electrolyte reservoir,
    the first cathode and the first anode are configured to be connectable to electronics, the first cathode and first anode configured to provide an electrical signal indicative of a level of oxygen in the sample gas, and the second anode and second cathode configured to prevent dissolved oxygen in the electrolyte reservoir from entering the main cell; and
    a flexible connector connected to the first cathode, the flexible connector sufficiently flexible and of a sufficient length to permit the first cathode to move vertically as a level of the electrolyte changes in the main cell.

11. An electrochemical oxygen sensor comprising:
    a main cell configured to hold an electrolyte and to receive a sample gas;

an electrolyte reservoir configured to contain a reserve of the electrolyte and fluidly connected to the main cell;

a first cathode configured to float on the electrolyte in the main cell;

a first anode configured to be in contact with the electrolyte in the main cell;

a second anode in contact with the electrolyte in the electrolyte reservoir; and a second cathode in contact with the electrolyte between the main cell and the electrolyte reservoir, the first cathode and the first anode are configured to be connectable to electronics, the first cathode and first anode configured to provide an electrical signal indicative of a level of oxygen in the sample gas, and the second anode and second cathode configured to prevent dissolved oxygen in the electrolyte reservoir from entering the main cell, and wherein the first cathode is configured to have, and to be in contact with, a surface area of 50% or more of a surface area of the electrolyte held by the main cell.

12. The electrochemical oxygen sensor of claim 11, wherein the first cathode is configured to have, and to be in contact with, a surface area of about 50% to about 90% of surface area of the electrolyte.

* * * * *